US008323348B2

(12) United States Patent
Lai et al.

(10) Patent No.: US 8,323,348 B2
(45) Date of Patent: Dec. 4, 2012

(54) BONE IMPLANTS

(75) Inventors: Wen-Fu T. Lai, Taipei (TW); Li-Chern Pan, Taipei (TW); Pau-Yee Lim, Hsinchu County (TW); Jung-Chou Oung, Hsinchu County (TW); Chun-Wei Chen, Taipei (TW)

(73) Assignee: Taiyen Biotech Co., Ltd., Taipei (TW)

( * ) Notice: Subject to any disclaimer, the term of this patent is extended or adjusted under 35 U.S.C. 154(b) by 110 days.

(21) Appl. No.: 11/063,074

(22) Filed: Feb. 22, 2005

(65) Prior Publication Data

US 2006/0190091 A1    Aug. 24, 2006

(51) Int. Cl.
*A61F 2/28* (2006.01)

(52) U.S. Cl. ....................................... 623/23.5

(58) Field of Classification Search ............... 623/11, 623/16, 22, 23, 18; 433/201.1
See application file for complete search history.

(56) References Cited

U.S. PATENT DOCUMENTS

| | | | | |
|---|---|---|---|---|
| 3,843,975 A * | 10/1974 | Tronzo | ........................ | 623/23.27 |
| 3,855,638 A * | 12/1974 | Pilliar | ........................ | 623/23.55 |
| 4,164,794 A * | 8/1979 | Spector et al. | ............... | 623/23.6 |
| 4,195,367 A * | 4/1980 | Kraus | ........................ | 623/23.49 |
| 4,362,681 A * | 12/1982 | Spector et al. | ............... | 264/112 |
| 4,483,678 A * | 11/1984 | Nishio et al. | ................ | 433/201.1 |
| 4,491,987 A * | 1/1985 | Park | ........................ | 623/23.59 |
| 4,542,539 A * | 9/1985 | Rowe et al. | ................ | 623/23.57 |
| 4,756,862 A * | 7/1988 | Spector et al. | ................ | 264/126 |
| 4,839,215 A * | 6/1989 | Starling et al. | ................ | 428/131 |
| 4,846,837 A * | 7/1989 | Kurze et al. | .................. | 623/23.6 |
| 4,904,266 A * | 2/1990 | Barber | ........................ | 623/23.36 |
| 5,080,671 A * | 1/1992 | Oron et al. | ..................... | 427/2.1 |
| 5,264,214 A * | 11/1993 | Rhee et al. | ..................... | 424/422 |
| 5,306,309 A * | 4/1994 | Wagner et al. | ............... | 623/17.16 |
| 5,348,788 A * | 9/1994 | White | .......................... | 428/131 |
| 5,356,433 A * | 10/1994 | Rowland et al. | ............. | 424/422 |
| 5,456,723 A | 10/1995 | Steinemann et al. | | |
| 5,652,056 A * | 7/1997 | Pepin | ........................ | 428/364 |
| 5,654,030 A * | 8/1997 | Munshi et al. | ................ | 427/2.24 |
| 5,683,443 A * | 11/1997 | Munshi et al. | ................ | 607/121 |
| 5,683,464 A * | 11/1997 | Wagner et al. | ............... | 623/17.16 |
| 5,700,479 A * | 12/1997 | Lundgren | ..................... | 424/435 |
| 5,876,444 A | 3/1999 | Lai | .................... | 623/11 |
| 6,008,431 A * | 12/1999 | Caldarise et al. | ............ | 623/23.3 |
| 6,156,064 A * | 12/2000 | Chouinard | ..................... | 623/1.44 |
| 6,306,925 B1 * | 10/2001 | Clupper et al. | ............... | 523/113 |
| 6,537,320 B1 * | 3/2003 | Michelson | ................ | 623/17.11 |
| 6,582,470 B1 * | 6/2003 | Lee et al. | ..................... | 623/23.55 |
| 2001/0018614 A1 * | 8/2001 | Bianchi | ..................... | 623/16.11 |
| 2001/0039454 A1 * | 11/2001 | Ricci et al. | ..................... | 623/23.5 |
| 2001/0044651 A1 * | 11/2001 | Steinke et al. | ............... | 623/1.16 |
| 2002/0062154 A1 * | 5/2002 | Ayers | ........................ | 623/23.76 |
| 2003/0003160 A1 * | 1/2003 | Pugh et al. | ..................... | 424/602 |
| 2003/0045942 A1 | 3/2003 | Lai et al. | | |
| 2003/0065401 A1 * | 4/2003 | Amrich et al. | ............. | 623/23.55 |
| 2003/0074081 A1 * | 4/2003 | Ayers | ........................ | 623/23.5 |
| 2003/0083646 A1 * | 5/2003 | Sirhan et al. | ............... | 604/891.1 |
| 2004/0110022 A1 * | 6/2004 | Pickrell et al. | ................ | 428/566 |
| 2004/0131754 A1 * | 7/2004 | Zitelli et al. | ................ | 427/2.24 |
| 2004/0153154 A1 | 8/2004 | Dinkelacker | | |
| 2004/0199241 A1 * | 10/2004 | Gravett et al. | ............... | 623/1.13 |
| 2005/0169964 A1 * | 8/2005 | Zitelli et al. | .................. | 424/423 |
| 2006/0019408 A1 * | 1/2006 | Waggoner et al. | ............. | 436/518 |
| 2006/0058888 A1 * | 3/2006 | Hunter et al. | ............... | 623/23.39 |
| 2006/0085063 A1 * | 4/2006 | Shastri et al. | ................ | 623/1.41 |
| 2006/0204542 A1 * | 9/2006 | Zhang et al. | .................. | 424/423 |

FOREIGN PATENT DOCUMENTS

| | | |
|---|---|---|
| CN | 1440731 A | 10/2003 |
| EP | 1 358 859 | 11/2003 |
| EP | 1358859 | 11/2003 |
| JP | 63-160662 | 7/1988 |
| JP | 2002-102329 | 4/2002 |
| JP | 2003-175098 | 6/2003 |
| WO | 96/16611 | 6/1996 |

OTHER PUBLICATIONS

Lacey et al., "Osteoprotegerin Ligand Is a Cytokine that Regulates Osteoclast Differentiation and Activation", Cell 93:165-176, 1998.
Amarante ES, de Lima LA, "Optimization of Implant Surfaces: Titanium Plasma spray and Acid-Etched Sandblasting—Current Status", Pesqui Odontol Bras. 15:166-173, 2001.
Bloebaum et al., "Porous-Coated Metal-Backed Patellar Components in Total Knee Replacement. A Postmortem Retrieval Analysis", J. Arthroplasty 8:195-202, 1993.
Branemark, "Osseointegration and its Experimental Background", Journal of Prosthetic Dentistry 50:399-410, 1983.
Chang et al., "Calcium and Phosphate Supplementation Promotes bone Cell Mineralization: Implications for Hydroxyapatite (HA)-enhanced Bone Formation", J. Biomed Mater Res. 52:270-278, 2000.

(Continued)

*Primary Examiner* — David Isabella
*Assistant Examiner* — Ann Schillinger
(74) *Attorney, Agent, or Firm* — Occhiuti Rohlicek & Tsao LLP

(57) ABSTRACT

This invention relates to a bone implant that includes a bio-inert substrate covered with a ceramic layer containing a plurality of indentations. The total surface area of the indentations is 30-70% of the total surface area of the ceramic layer. This invention also relates to a method of preparing such a bone implant. The method includes: (1) affixing a ceramic layer on the surface of a bioinert substrate; (2) forming a plurality of indentations in the ceramic layer, wherein the total surface area of the indentations is 30-70% of the total surface area of the ceramic layer; and (3) immobilizing a biopolymer onto the ceramic layer via covalent bonding.

23 Claims, No Drawings

OTHER PUBLICATIONS

Chao et al., "Histologic Study of Tissue Response to Implanted Hyrdorxylapatite in Two Patients", J. Oral Maxillotac Surg 45:359-362, 1987.

Cook et al., "Hydroxyapatite-Coated Porous Titanium for Use as an Orthopedic Biologic Attachment System", Clin Orthop 30:303-312, 1988.

Cook et al., "Inflammatory Response to Retrieved Noncemented Porous-Coated Implants", Clin Orthop 264:209-222, 1991.

Dalton et al., "In Vivo Mechanical and Histological Characteristics of HA-coated Implants Vary with Coating Vendor", Journal of Biomedical Materials Research 29:239-245, 1995.

Geesink et al., "Bonding of Bone to Apatite-Coated Implants", J. Bone Jt Surg 70B-17-22, 1988.

Geesink, "Hydroxyapatite-Coated Total Hip Prostheses", Clin Orthop 261:39-58, 1990.

Kent et al., "Alveolar Ridge Augmentation Using Nonresorbable Hydroxylapatite with or without Autogenous Cancellous Bone", J. Oral Maxillofac Surg 41:629-642, 1983.

Burke, "Dissolution Kinetics of Calcium Phosphate Coatings", Implant Dent. 7:323-30, 1998.

Mehlisch et al., "Evaluation of Collagen/Hydroxylapatite Augmenting Deficient Alveolar Ridge", J. Oral Maxillofac Surg 45:408-413, 1987.

Overgaard et al., "Resorption of Hydroxyapatite and Fluorapatite Ceramic Coatings on Weight-bearing Implants: A Quantitative and Morphological Study in Dogs", J. Biomed Mater Res. 39:141-152, 1998.

Remacle et al., "Tissue Integration of the Collagen-Hydroxylapatite Implant: Histological Examination in Canine Bone and Surrounding Tissues", European Archives of Oto-Rhino-Laryngology 337-341, 1991.

Rokkum et al., "HA Particles Can be Released from Well-Fixed HA-Caoted Stems", Acta Orthop Scand 73:298-306, 2002.

Rothstein et al., "Use of Hydroxylapatite for the Augmentation of Deficient Alveolar Ridges", J. Oral Maxillofac Surf 42:224-230, 1984.

* cited by examiner

BONE IMPLANTS

BACKGROUND

Loosening of implants from bone tissues is a major concern in reconstructive surgery and joint replacement. The cause has been attributed to a layer of fibrous tissues developed around the implant that diminishes the integrity and mechanical stability of the implant/bone interface. During the 1950s, it was shown that titanium could become permanently incorporated into bones, a process now known as osseointegration. An osseointegrated implant is characterized by lack of relative movement and absence of soft tissues between the implant and the bone. See, e.g., Branemark, (1983) *J. Prosthet. Dent.* 50: 399-410. The surface of an implant can be coated with osteoconductive materials to further enhance osseointegration of the implant. Although many bone implants are now available on the market, there still exists a need to develop an implant with superior osseointegration.

SUMMARY

This invention is based on an unexpected discovery that an indented hydroxyapatite coating on a bone implant promotes osseointegration.

In one aspect, this invention features a bone implant that includes a bioinert substrate covered with a ceramic layer (e.g., a hydroxyapatite layer) containing a plurality of indentations. The total surface area of the indentations is 30-70% (e.g., 50-60%) of the total surface area of the ceramic layer. The total surface area of the indentations is the sum of the opening surface areas of all indentations. The total surface area of the ceramic layer is the sum of the total surface area of the indentations and the unindented surface area.

The bioinert substrate can be made of a variety of materials, such as metals (e.g., titanium or titanium alloys) and ceramic materials (e.g., porcelain). Preferably, a portion of the surface of the bioinert substrate contains small ridges having widths of 10-30 μm (e.g., 15-20 μm) and heights of 10-30 μm (e.g., 15-20 μm) and another portion of the surface contains large ridges having widths of 60-100 μm (e.g., 70-90 μm) and heights of 40-80 μm (e.g., 50-70 μm). When the bioinert substrate is made of a metal or a metal alloy, its surface can be oxidized to form a layer of a metal oxide or metal oxides.

The ceramic layer preferably covers the surface of the bioinert substrate having the large ridges, but not the surface having the small ridges. The ceramic layer can be composed of an inorganic material, such as hydroxyapatite. The surface of the ceramic layer can also be immobilized with a biopolymer via covalent bonding. Examples of suitable biopolymers include protein (e.g., collagen) or protein-containing macromolecules (e.g., proteoglycan). Such biopolymers can function as a scaffold for cell attachment and migration to facilitate regeneration of new bone tissues. If desired, a bone formation promoter (e.g., osteoprotegerin) can also be covalently bonded to the ceramic layer. A bone formation promoter promotes growth of bone tissues and maintenance of bone mass.

In another aspect, this invention features a method of preparing a bone implant. The method includes three steps: (1) affixing a ceramic layer on the surface of a bioinert substrate, the surface of which can be pre-treated; (2) forming a plurality of indentations in the ceramic layer, wherein the total surface area of the indentations is 30-70% of the total surface area of the ceramic layer; and (3) immobilizing a biopolymer onto the ceramic layer via covalent bonding. Before the affixing step, the bioinert substrate can be treated to form small ridges having widths of 10-30 μm and heights of 10-30 μm on one portion of the surface, and to form large ridges having widths of 60-100 μm and heights of 40-80 μm on another portion of the surface. Preferably, the bioinert substrate is made of a titanium alloy and its surface is oxidized to form a layer of metal oxides before the affixing step.

The details of one or more embodiments of the invention are set forth in the description below. Other features, objects, and advantages of the invention will be apparent from the description and from the claims.

DETAILED DESCRIPTION

This invention relates to a bone implant that includes a bioinert substrate covered by a biodegradable ceramic layer containing a plurality of indentations.

The bioinert substrate can be prepared from a variety of materials, such as metals and ceramic materials. Typically, titanium or its alloy is used. Titanium is a bioinert material that facilitates osseointegration. Titanium and its alloy are either commercially available or can be prepared by well-known methods.

The surface of the bioinert substrate can be treated to form specific roughness patterns (e.g., small ridges on one portion of the surface and large ridges on another). The surface treatment can be carried out by mechanical, chemical, and electrochemical methods, as well as other suitable methods well known in the art. Typically, small ridges can be generated by chemical etching or plasma spray. See, e.g., Ronold et al., (2003), *Biomaterials* 24:4559; Jonasova et al., (2004) *Biomaterials* 25:1187; and Prado da Silva et al., (2000) *Mat. Res.* 3(3): 61. Large ridges can be generated by techniques such as grit blasting, abrasive excimer laser treatment, water jet peening, and electrochemical micro-machining. See, e.g., GonzaAlez-GarcoAa et al., (1999) *Thin Solid Films* 352:49; Mellali et al., (1996) *Surface and Coatings Technology* 81:275; Bereznai et al., (2003) *Biomaterials,* 24:4197; Arola et al., (2002) *Wear,* 249:943; and Madore et al., (1997) *J. Micromech. Microeng.,* 7:270.

For example, the entire surface can be first annealed at a high temperature (e.g., about 800° C. or higher) for a certain period of time at atmospheric pressure in a gas furnace, followed by cooling down to room temperature. The surface can then be etched in an acid solution for a predetermined period of time slightly above room temperature to form small ridges having widths of 10-30 μm and heights of 10-30 μm. Subsequently, the surface at the top portion can be covered (e.g., with an anti-corrosive tape). The remaining portion of the surface can then be further etched in a more concentrated acid solution for a longer period of time at a higher temperature to form large ridges having widths of 60-100 μm and heights of 40-80 μm. The surface of the substrate thus obtained contains a portion having small ridges (e.g., the top portion of the surface) and the remaining portion having large ridges. When in use, the substrate can be placed at an implantation site such that the portion having small ridges is placed outward (e.g., contacting the epithelial layer) and the portion having large ridges is placed inward (e.g., contacting the bone). The small ridges facilitate fibroblast proliferation and reduce bacterial infection. The large ridges facilitate adhesion of osteoblasts. If desired, a substrate (e.g., a Ti alloy) can be oxidized to form a layer (e.g., 5-10 μm) of metal oxides (e.g., $TiO_2$), which prevents or slows the corrosion to the substrate.

The biodegradable ceramic layer can be composed of inorganic materials, such as hydroxyapatite. Hydroxyapatite, naturally occurring in, bones, enamel, or dentin, has been used for years as a bone substitute or a coating material. See, for example, Frame (1987) *Int. J. Oral Maxillofacial Surgery* 16: 642-55, and Parsons et al. (1988) *Annals N.Y. Academy of Sciences* 523: 190-207. Hydroxyapatite can be prepared by well-known methods or purchased from commercial suppliers. It is either a pure compound of $Ca_{10}(PO_4)_6(OH)_2$, or a composition containing other ions, such as carbonate, fluoride, chloride, or barium. A hydroxyapatite-based ceramic layer can be formed by applying hydroxyapatite on the surface of a substrate by, e.g., plasma-spraying, sol-gel processing, ion beam or radio frequency sputtering, pulsed laser deposition, hot isostatic pressing, and electrophoretic deposition. See, e.g., Geesnik et al., (1990) *Clin. Orthop.* 261: 39-58; Ratner et al., "Plasma Deposition and Treatment for Biomedical Applications" in *Plasma Depostion, Treatment, and Etching of Polymers*, edited by R. d'Agostino, Academic Press, Inc., 1990; and Kawakami et al., (1998) *Biotechnology and Bioengineering*, 32:369-373. Typically, the thickness of the hydroxyapatite-based ceramic layer ranges from 25-70 μm. Such a layer, which promotes bone apposition, is preferably applied to the surface of the substrate having large ridges. To achieve this, the surface having small ridges can be covered before applying the hydroxyapatite-based ceramic layer on the substrate so that only the surface having large ridges is coated with the ceramic layer.

Indentations in the ceramic layer can be formed by removing parts of the ceramic layer by a mechanical method (e.g., sand blasting or grit blasting), or other suitable methods. These indentations typically have a cylindrical profile and typically have diameters ranging from 350-650 μm (e.g., 400-600 μm). In the indentations, the ceramic materials are generally completely removed and the substrate is exposed. The indentations facilitate the recruitment and the retention of osteoblasts. The indentations may be evenly or randomly distributed in the ceramic layer.

The ceramic layer can be covalently bonded with a biopolymer (e.g., a collagen-based biopolymer) to facilitate new bone growth. For example, the surface of the ceramic layer is first modified with a functional group, such as amino or hydroxyl. The functional groups can be introduced by plasma deposition or chemical priming. Materials used in plasma deposition include ammonia plasma, allylamine plasma, allylalcohol plasma, and plasma of any gas containing amino, hydroxyl, or other reactive groups. Compounds used in chemical priming include amino silanes, hydroxyl silanes, or other silanes containing amino, hydroxyl, or other reactive groups. See, e.g., Sano et al. (1993) *Biomaterials* 14: 817-822; and Wang and Hsiue (1993) *J. Polymer Science, Part A: Polymer Chemistry* 31: 2601-2607. Typically, both the surface of the ceramic layer and the surface of the bioinert substrate exposed by the indentations in the ceramic layer are modified with a functional group.

Collagen is an example of a biopolymer that can be used in an implant of this invention. Collagen, e.g., type I collagen, can be isolated from human or animal tissues, such as tendon, skin, bone, or ligament. See, for example, Miller and Rhodes, (1982) *Methods in Enzymology* 82: 33-64. It can be purified by a method of retaining the telopeptide (e.g., U.S. Pat. No. 3,114,593), or alternatively, by a method of removing the telopeptide (e.g., U.S. Pat. No. 4,233,360). It can also be reconstituted by cross-linking using a chemical reagent (e.g., U.S. Pat. Nos. 5,876,444 and 6,177,514) or by other means (e.g., UV light). Collagen can be covalently bonded to a hydroxyapatite-based ceramic layer. The covalent bond can be formed directly between a functional group in collagen (e.g., carboxylate) and a functional group in modified hydroxyapatite (e.g., amino), or formed indirectly through a third molecule, e.g., a cross-linker. A cross-linker is a reagent that has at least two functional groups, one of which can form a bond with the biopolymer and the other with the modified hydroxyapatite. Examples of cross-linkers include glutaraldehyde, epichlorohydrin, tresyl chloride, and N-hydroxysuccinimide.

The ceramic layer can be further covalently bonded with a bone formation promoter, such as osteoprotegerin. Osteoprotegerin has been described in U.S. Application Publication No. 2003-0045942 and references cited therein. It can be attached to the ceramic layer together with collagen, e.g., by immersing a substrate having a ceramic layer in a solution containing both collagen and osteoprotegerin for an adequate period of time. The substrate can then be pulled out of the solution and dried by either air-drying or freeze drying. Alternatively, it can be attached to the ceramic layer by immersing a substrate having a ceramic layer in a solution containing osteoprotegerin after collagen is immobilized on the ceramic layer.

As an example, a bone implant of this invention can be prepared as follows: The entire surface of a titanium alloy substrate is first etched in a HCl aqueous solution to form small ridges. The surface is further annealed to form large ridges except at the top section of the substrate. Subsequently, the entire surface of the substrate is blasted with oxygen to form a layer of metal oxides. A layer of hydroxyapatite is coated on the surface having the large ridges by plasma-spraying. Parts of the hydroxyapatite layer are then removed by sand blasting or grit blasting, thereby forming a plurality of indentations. The surface is then functionalized with amino or hydroxyl. Collagen is subsequently immobilized on the surface by reacting the functional groups on the collagen with the functional groups on the surface. The surface can be further modified with osteoprotegerin by the same method.

A bone implant of this invention can be used to repair bone defects (such as alveolar bone defects) by following standard surgical procedures.

The specific example below is to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety.

EXAMPLE 1

Preparation of Materials

Preparation of a Porous Hydroxyapatite-Based Matrix.

Hydroxyapatite powder is prepared by a wet chemical method involving the reaction: $10Ca(NO_3)_2 + 6(NH_4)_3PO_4 + 2NH_3 \cdot H_2O + Ca_{10}(PO_4)_6(OH)_2 + 20NH_4NO_3$. A porous hydroxyapatite-based matrix is prepared by the following steps: (i) preparing a slurry, which includes hydroxyapatite powder, silicon carbide, magnesia, and water; (ii) molding a network substrate (e.g., polyurethane, polyvinyl chloride, or polyethyleneglycol) into a desired shape; (iii) coating the slurry onto the network substrate; and (iv) removing extra slurry by centrifugation. If necessary, steps (i)-(iv) are repeated. The thus obtained hydroxyapatite-containing substrate is sintered at a temperature of 1200° C. and then cooled down. The temperature is increased slowly so that the network substrate is decomposed gradually and no cracks are formed. Thus, a porous hydroxyapatite-based matrix is obtained, with an average pore size of 200-350 μm. After washing, the matrix is sterilized by gamma ray irradiation (20 kGy).

Extraction and Purification of Type I Collagen.

Type I collagen is extracted and purified from tendons of New Zealand white rabbits or other suitable mammals. The tendons are dissected, sliced, and washed with several changes of cold distilled water to remove plasma proteins, and then extracted by constant stirring overnight at 4° C. with 0.5 M NaCl in 50 mM Tris-HCl, pH 7.4. The supernant is decanted and the reminder is washed with several changes of cold distilled water to remove salts and then incubated overnight at 4° C. with 0.5 M HOAc pH 2.5 to obtain an aqueous extract. A salt solution (0.9 M NaCl) is added to the extract, causing precipitation. The precipitation is collected by centrifugation at 13,000 rpm for 30 min, and dissolved in 0.05 M HOAc to form a collagen-containing solution. Another salt solution (0.02 M $Na_2HPO_4$) is added twice to the collagen-containing solution over a 24 to 48 hr period causing precipitation. The precipitation is collected by centrifugation, and dissolved in 50 mM HOAc to obtain another collagen-containing solution. The collagen-containing solution is dialyzed against 5 mM HOAc, and finally lyophilized.

EXAMPLE 2

Preparation of a Bone Implant

Threaded substrates were purchased from Crucible Materials Corporation, Pittsburgh, Pa., USA. The substrates were made of a titanium alloy (Ti6Al4V), and had diameters ranging from 3.25 mm to 5.0 mm and lengths ranging from 8 mm to 18 mm. The surface of the substrates was first annealed at 870-1050° C. for 1-3 hours at atmospheric pressure in a gas furnace and then cooled down to room temperature. The surface was then etched in a 1-3 M HCl aqueous solution at 30-50° C. for 1-3 hours to form small ridges (i.e., having widths of 10-30 μm and having heights of 10-30 μm). The surface at the top 2-3 mm portion was then covered with an anti-corrosive tape. The remaining surface was then further etched in a 1-6 M HCl aqueous solution at 50-90° C. for 3-6 hours to form large ridges (i.e., having widths of 60-100 μm and heights of 40-80 μm). The surface was then blasted with oxygen to form a layer of metal oxides having a thickness of 5-10 μm. The substrates thus obtained were coated with a layer of hydroxyapatite using a plasma-spraying technique. The thickness of the hydroxyapatite layer is about 40-50 μm. Parts of the hydroxyapatite layer were then removed by sand blasting, thereby forming a plurality of indentations. The diameters of the indentations range from 400 μm to 600 μm. The substrates thus obtained were functionalized with amino and then linked with collagen.

EXAMPLE 3

Calcium Deposition Assay

Six disks were tested for calcium deposition: (1) RT: an untreated titanium alloy disk, (2) RT-HCl: a titanium alloy disk etched with HCl to form small ridges, (3) RT-950-HCl: a titanium alloy disk annealed at 950° C., and etched with HCl to form large ridges, (4) RT-950-HCl-$TiO_2$: a titanium alloy disk annealed at 950° C., etched with HCl to form large ridges, and oxidized to form a layer of metal oxides, (5) RT-950-HCl-$TiO_2$-HAF: a titanium alloy disk annealed at 950° C., etched with HCl to form large ridges, oxidized to form a layer of metal oxides, and fully coated with a layer of hydroxyapatite, and (6) RT-950-HCl-$TiO_2$-HAP: a titanium alloy disk annealed at 950° C., etched with HCl to form large ridges, oxidized to form a layer of metal oxides, and partially coated with a layer of hydroxyapatite. The disks had diameters ranging from 2-3 cm and thickness ranging from 3-5 mm.

U2 osteoblasts were obtained from a human osteosarcoma and cultured on each of the above disks placed in a 6-well plate in McCoy's 5A medium containing 10% fetal bovine serum (FBS) and 5% antibiotics at 37° C. The medium was changed after cultivation for 4 days. After cultivation for 4 more days, the calcium content in the medium for each disk was determined. More calcium deposition was noted in the media for RT-950-HCl-$TiO_2$-HAP, RT-950-HCl-$TiO_2$-HAF, and RT-950-HCl-$TiO_2$ than that in the media for RT, RT-HCl, and RT-950-HCl. The results suggest that more calcium was deposited on the surface of RT-950-HCl-$TiO_2$-HAP, RT-950-HCl-$TiO_2$-HAF, and RT-950-HCl-$TiO_2$ than that deposited on the surface of RT, RT-HCl, and RT-950-HCl.

EXAMPLE 4

Osteoblasts Deposition Assay

The six disks mentioned in Example 3 were also tested in an osteoblast deposition assay. U2 osteoblasts obtained from a human osteosarcoma were cultured on each disk placed in a 6-well plate in McCoy's 5A medium containing 10% FBS and 5% antibiotics at 37° C. The medium was removed after cultivation for 4 days. The surface of each disk was observed under an electronic microscope. Few osteoblasts appeared on the surface of RT, as most osteoblasts were removed from the RT surface after removing the medium. A few osteoblasts were observed on the RT-HCl surface. Similar to RT, most osteoblasts on the RT-HCl surface were removed after removing the medium. A significant amount of osteoblasts were deposited on the large ridges of the RT-950-HCl surface. A significant amount of osteoblasts were also deposited on the large ridges of the metal oxide layer of RT-950-HCl-$TiO_2$. Compared to RT-950-HCl and RT-950-HCl-$TiO_2$, more osteoblasts were deposited on the large ridges of the metal oxide layer of RT-950-HCl-$TiO_2$-HAF. Compared to RT-950-HCl-$TiO_2$-HAF, more osteoblasts were deposited on the large ridges of the metal oxide layer of RT-950-HCl-$TiO_2$-HAP.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A bone implant comprising a bioinert substrate that includes a surface having a first portion and a second portion, the first portion containing small ridges, each of which has a width of 10-30 μm and a height of 10-30 μm, and the second portion containing large ridges, each of which has a width of 60-100 μm and a height of 40-80 μm, wherein the bone implant is configured such that, when it is placed at an implant site in a subject, the second portion is in contact with a bone.

2. The bone implant of claim 1, wherein each of the large ridges has a width of 70-90 μm and a height of 50-70 μm.

3. The bone implant of claim 1, wherein each of the small ridges has a width of 15-20 μm and a height of 15-20 μm.

4. The bone implant of claim 1, wherein the bioinert substrate is a metal-based substrate.

5. The bone implant of claim 4, wherein the substrate is a titanium alloy-based substrate.

6. The bone implant of claim 4, further comprising a metal oxide layer disposed on the bioinert substrate.

7. The bone implant of claim 6, wherein the second portion is covered with a ceramic layer that contains a plurality of indentations, the indentations occupying 30-70% of the total surface of the ceramic layer.

8. The bone implant of claim 7, wherein the ceramic layer is a hydroxyapetite layer.

9. The bone implant of claim 7, wherein the biopolymer is a collagen-based biopolymer.

10. The bone implant of claim 1, wherein the second portion is covered with a ceramic layer that contains a plurality of indentations, the indentations occupying 30-70% of the total surface of the ceramic layer.

11. The bone implant of claim 10, wherein the indentations occupy 50-60% of the total surface of the ceramic layer.

12. The bone implant of claim 10, wherein the ceramic layer is a hydroxyapetite layer.

13. The bone implant of claim 10, further comprising a biopolymer covalently bonded to the ceramic layer.

14. The bone implant of claim 10, further comprising a bone formation promoter covalently bonded to the ceramic layer.

15. A method of preparing a bone implant, comprising:
obtaining a bioinert substrate that has a surface with a first portion and a second portion, and,
forming on the first portion small ridges, each of which has a width of 10-30 μm and a height of 10-30 μm, and on the second portion large ridges, each having a width of 60-100 μm and a height of 40-80 μm,
wherein the bone implant is configured such that, when it is placed at an implant site in a subject, the second portion is in contact with a bone.

16. The method of claim 15, wherein the bioinert substrate is a metal-based substrate.

17. The method of claim 16, wherein the substrate is a titanium alloy-based substrate.

18. The method of claim 16, after the forming step, further comprising oxidizing the surface of the bioinert substrate to form a layer of metal oxides.

19. The method of claim 18, after the oxidizing step, further comprising:
affixing a ceramic layer on the second portion, and
generating a plurality of indentations in the ceramic layer, wherein the indentations occupy 30-70% of the total surface of the ceramic layer.

20. The method of claim 19, wherein the ceramic layer is a hydroxyapetite layer.

21. The method of claim 19, after the generating step, further comprising immobilizing a biopolymer onto the ceramic layer via covalent bonding.

22. The method of claim 21, wherein the biopolymer is a collagen-based biopolymer.

23. The method of claim 19, after the generating step, further comprising covalently linking a bone formation promoter to the ceramic layer.

* * * * *